US012685657B2

(12) United States Patent
Hall et al.

(10) Patent No.: US 12,685,657 B2
(45) Date of Patent: Jul. 21, 2026

(54) ANKLE FOOT ORTHOSIS

(71) Applicants: Martha Hall, Landenberg, PA (US);
Elisa Sarah Arch, Garnet Valley, PA
(US); Ahlad Neti, Enola, PA (US);
Ashutosh D. Khandha, Wilmington,
DE (US)

(72) Inventors: Martha Hall, Landenberg, PA (US);
Elisa Sarah Arch, Garnet Valley, PA
(US); Ahlad Neti, Enola, PA (US);
Ashutosh D. Khandha, Wilmington,
DE (US)

(73) Assignee: University of Delaware, Newark, DE
(US)

( * ) Notice: Subject to any disclaimer, the term of this
patent is extended or adjusted under 35
U.S.C. 154(b) by 140 days.

(21) Appl. No.: 18/275,063

(22) PCT Filed: Feb. 11, 2022

(86) PCT No.: PCT/US2022/016126
§ 371 (c)(1),
(2) Date: Jul. 31, 2023

(87) PCT Pub. No.: WO2022/174039
PCT Pub. Date: Aug. 18, 2022

(65) Prior Publication Data
US 2024/0130881 A1 Apr. 25, 2024
US 2024/0225876 A9 Jul. 11, 2024

Related U.S. Application Data

(60) Provisional application No. 63/148,722, filed on Feb.
12, 2021.

(51) Int. Cl.
_A61F 5/01_ (2006.01)
(52) U.S. Cl.
CPC .................................. _A61F 5/0113_ (2013.01)

(58) Field of Classification Search
CPC .... A61F 5/0111; A61F 5/0113; A61F 5/0585;
A61F 5/0104; A43B 7/20
See application file for complete search history.

(56) References Cited

U.S. PATENT DOCUMENTS

| | | | | | |
|---|---|---|---|---|---|
| 325,280 | A | * | 9/1885 | Smadbeck | ................ A43B 7/20 |
| | | | | | 36/89 |
| 2,712,310 | A | | 7/1955 | Giambra | |
| 2,994,322 | A | * | 8/1961 | Cullen | .................. A61F 5/0111 |
| | | | | | 450/41 |
| 3,859,991 | A | * | 1/1975 | Theodores | ............ A61F 5/0113 |
| | | | | | 602/28 |
| 6,790,193 | B2 | | 9/2004 | Wellershaus et al. | |

(Continued)

FOREIGN PATENT DOCUMENTS

| | | |
|---|---|---|
| CN | 109998759 A | 7/2019 |
| DE | 102013019079 A1 | 5/2015 |

(Continued)

OTHER PUBLICATIONS

International Preliminary Report on Patentability for International
Application No. PCT/US2022/016126, dated Aug. 15, 2023, 7
pages.

(Continued)

_Primary Examiner_ — Alireza Nia
_Assistant Examiner_ — Gina Mccarthy
(74) _Attorney, Agent, or Firm_ — Buchanan Ingersoll &
Rooney PC

(57) ABSTRACT

An ankle-foot orthosis having a foot plate defining a foot bed
contoured to underlie the foot of the wearer, a flexible cuff
configured to wrap around at least a portion of the shank of
the wearer, and a strut assembly comprising a plurality of
metal wires connecting the foot plate to the cuff. The
plurality of metal wires may include piano wires. The foot
plate may be fabricated with a computer aided manufactur-
ing process.

14 Claims, 8 Drawing Sheets

(56) References Cited

U.S. PATENT DOCUMENTS

| | | | |
|---|---|---|---|
| 8,323,224 B2 | 12/2012 | Shlomovitz | |
| 9,962,279 B2 | 5/2018 | Haley et al. | |
| 10,357,390 B2 | 7/2019 | McGovern et al. | |
| 11,083,614 B2 | 8/2021 | Hassel | |
| 2006/0196021 A1* | 9/2006 | Touzov | A43C 1/00 |
| | | | 24/712 |
| 2006/0270958 A1 | 11/2006 | George | |
| 2015/0150709 A1 | 6/2015 | Ljubimir et al. | |
| 2015/0328840 A1 | 11/2015 | Zachariasen et al. | |
| 2016/0081839 A1 | 3/2016 | Hassel et al. | |
| 2018/0343981 A1* | 12/2018 | Hanft | A61B 5/1036 |
| 2019/0232592 A1* | 8/2019 | Tran | A43D 1/02 |
| 2020/0275736 A1* | 9/2020 | Hernandez Garcilazo | |
| | | | A43B 13/125 |
| 2020/0375776 A1 | 12/2020 | Thor et al. | |
| 2021/0386575 A1 | 12/2021 | Blanck | |

FOREIGN PATENT DOCUMENTS

| | | |
|---|---|---|
| WO | 2011128588 A1 | 10/2011 |
| WO | 2021055533 A1 | 3/2021 |

OTHER PUBLICATIONS

International Search Report and Written Opinion for International Application No. PCT/US2022/016126, dated May 2, 2022, 7 pages.

Neti, Thesis for Development of a Novel AFO Design Incorporating User, Perspective and Medical Purpose, 2020, 70 pages.

Wouters EJM, et al., Use of and Satisfaction with Ankle Foot Orthoses. Clin Res Foot Ankle. 2015:3(1):1-8.

Peethambaran A., et al., The Relationship between Performance, Satisfaction, and Well Being for Patients Using Anterior and Posterior Design Knee-ankle-foot-orthosis. JPO J Prosthetics Orthot. 2000;12(1):33-45.

Fisher LR, Mclellan DL. Questionnaire Assessment of Patient Satisfaction with Lower Limb Orthoses from a District Hospital. Prosthetics and Orthotics International, vol. 13. 1989, 7 pages.

O'Connor J, McCaughan D, McDaid C, et al. Orthotic management of instability of the knee related to neuromuscular and central nervous system disorders: systematic review, qualitative study, survey and costing analysis. 2019, 10 pages.

* cited by examiner

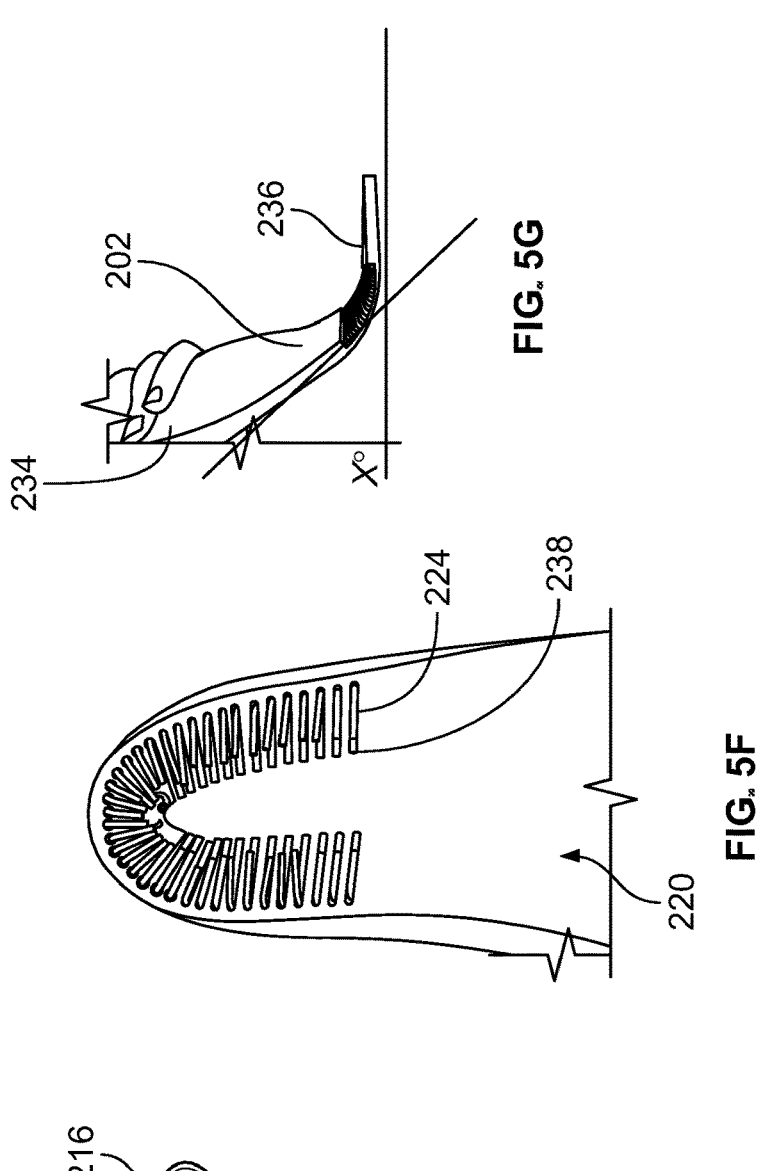
FIG. 5G
FIG. 5F
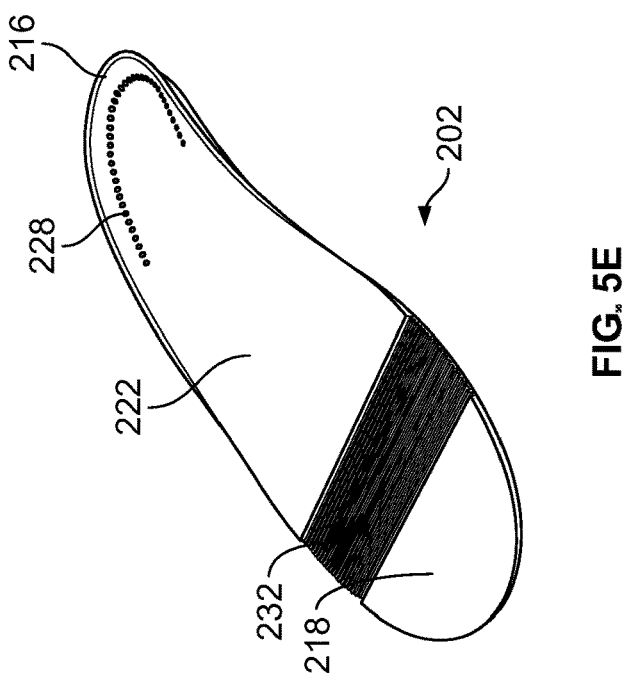
FIG. 5E

ANKLE FOOT ORTHOSIS

CROSS REFERENCE TO RELATED APPLICATIONS

This application is a U.S. National Phase Patent Application of PCT Patent Application No. PCT/US2022/016126, filed Feb. 11, 2022, which is related to and claims priority from U.S. Provisional Application Ser. No. 63/148,722, titled FUNCTIONAL FASHION AFO, filed Feb. 12, 2021, the contents of both of which are incorporated herein by reference in their entireties for all purposes.

FIELD OF THE INVENTION

The present invention relates generally to orthopedic and orthotic devices, and more particularly, to ankle-foot-or-thoses (AFOs) for use in facilitating and managing mobility issues.

BACKGROUND OF THE INVENTION

A medical stroke occurs often among the elderly population, particularly for individuals over age 65. Post-stroke patients frequently suffer from hemiparesis and related chronic mobility issues. Foot drop (or drop foot), caused by muscle weakness of plantar flexors and/or dorsi flexors, is a common gait abnormality among hemiparesis patients. The "foot drop" condition may affect either the right, or left foot, and sometimes both feet are affected. If both feet are affected, walking is very difficult, such that the patient may shuffle their feet or drag their toes, and may use other devices, such as canes or walkers.

Conventionally, as part of the stroke recovery/rehabilitation process, patients can improve their mobility, general independence, and overall quality of life via use of an ankle-foot-orthosis (AFO). An AFO is generally configured to support the ankle joint and stabilize the corresponding tissues, thereby preventing unwanted movement of the ankle joint. However, AFOs are often bulky, uncomfortable, unappealing, expensive, and generally do not have a user-centered focus.

With reference to the drawings, FIGS. 1A-1H are images of examples of prior art AFOs. FIG. 1A is an image of a typical AFO model made of plastic, such as FREEDOM® Swedish AFO, as described and designed by AliMed, Inc. of Dedham, Massachusetts. This AFO is usually very flimsy and offer very limited support. FIG. 1B shows another model of AFO, such as SaeboStep, as described and designed by Saebo of Charlotte, North Carolina, where an ankle cuff is linked to a shoe to hold it up. This model may prevent foot drop, but it nevertheless fails to address the dorsi flexion weakness found in hemiparesis patients. FIG. 1C displays yet another AFO model, such as the Heelift AFO (Ankle Foot Orthosis)—Smooth Foam Interior, as described and designed by AliMed, Inc. of Dedham, Massachusetts, which is configured for maximum cushion and stabilization, but is nonetheless excessively bulky and large for every day use. Other prior art AFOs include Type C-50 Heavy-Duty AFO (FIG. 1D), as described and designed by AliMed, Inc. of Dedham, Massachusetts; FREEDOM® Soft Foot Drop Brace (FIG. 1E), as described and designed by AliMed, Inc. of Dedham, Massachusetts; AFO Brace Medical Ankle Foot Orthosis Support Drop Foot Postural Correction Brace (Right/S) (FIG. 1F), as manufactured by Furlove; FREE-DOM® Adjustable Foot Drop Brace (FIG. 1G), as described and designed by AliMed, Inc. of Dedham, Massachusetts;

Core Products FootFlexor AFO Foot Drop Brace—Universal (FIG. 1H), as described and designed by Core Products International, Inc. of Osceola, Wisconsin.

However, a common issue among prior art AFO products is the lack of adaptability to individuals of varying anthropometric shapes, including among hemiparesis patients during their recovery or rehabilitation process. Further, prior art AFOs may be cost prohibitive to some patients, thereby affecting the level of treatment or rehabilitation received. Assessments of existing AFO products were performed to determine the limitations of existing AFOs for facilitating and managing mobility issues, such as foot drop. Each product was assessed based on comfort, sizing, appearance, functionality, likes, and dislikes. The exemplary prior art AFOs that were evaluated were:

1. Dr. Arch's initial AFO
2. Heelift
3. Alimed 64105LF, Freedom foot drop brace
4. Foot flexor Core Products
5. Mandarin
6. AliMed Ankle Wrap
7. SaeboStep Thus, improved AFO systems and devices are desired for improving rehabilitation and health outcomes by creating a discrete, simple, minimalistic design that can easily be incorporated into many types of footwear, while also providing enough support to allow for ambulation and overall mobility.

SUMMARY OF THE INVENTION

Aspects of the present invention are directed to orthopedic and orthotic devices, and more particularly, to ankle-foot-orthoses for use in facilitating and managing certain mobility issues.

In accordance with one aspect of the present invention, an ankle-foot orthosis configured to be worn by a target wearer comprises a foot plate having a foot bed contoured to underlie a foot of the target wearer, a flexible cuff configured to wrap around at least a portion of a shank of the target wearer, and a strut assembly comprising a plurality of metal wires connecting the foot plate to the cuff.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIGS. 5E-5G are images depicting the exemplary foot plate associated with the exemplary AFO of FIG. 5A.

DETAILED DESCRIPTION OF THE INVENTION

Figures 1A, 1B, 1C:
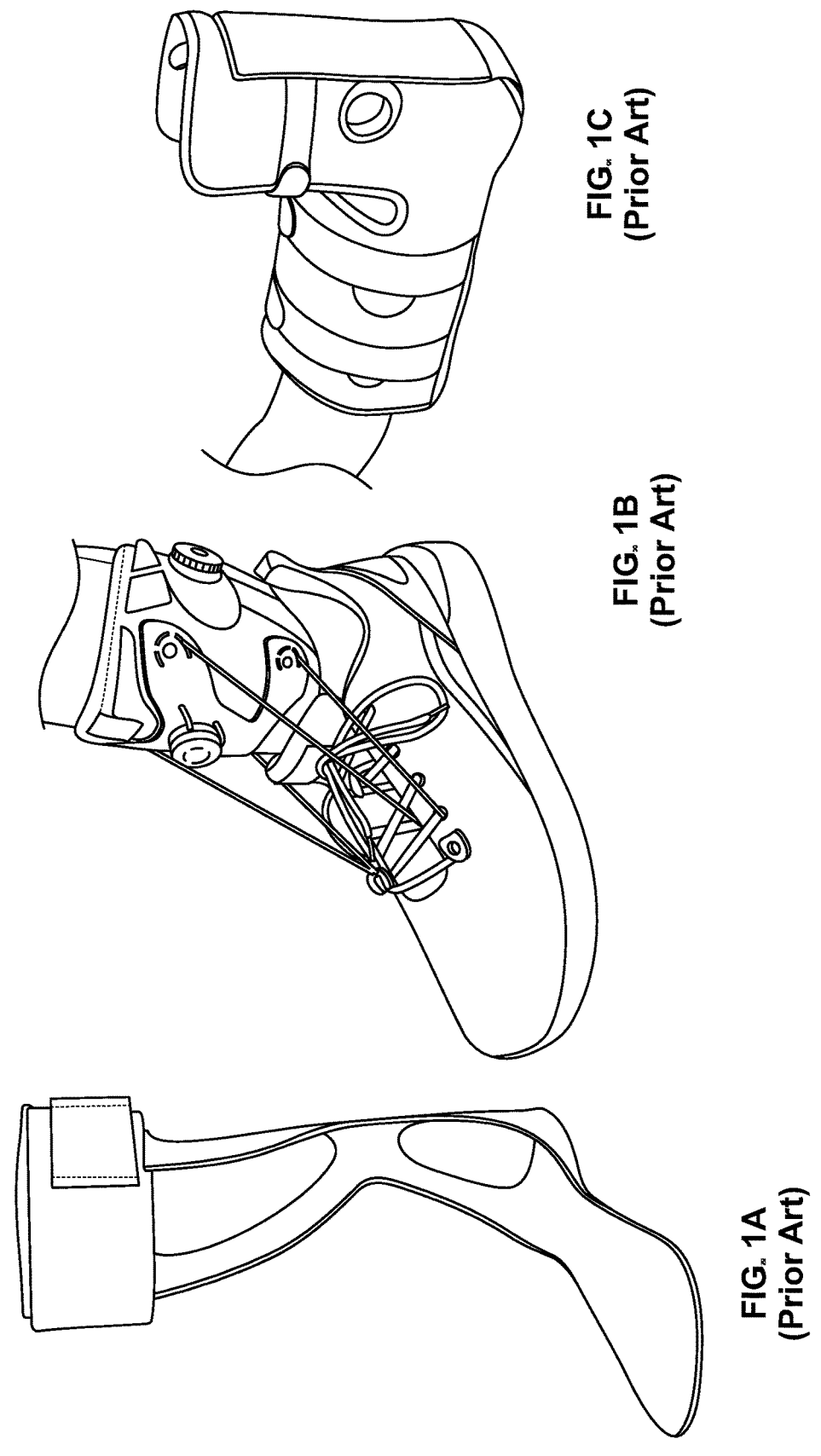
FIGS. 1A-1H are images depicting AFOs in accordance with prior art.
Figures 1D, 1E, 1F:
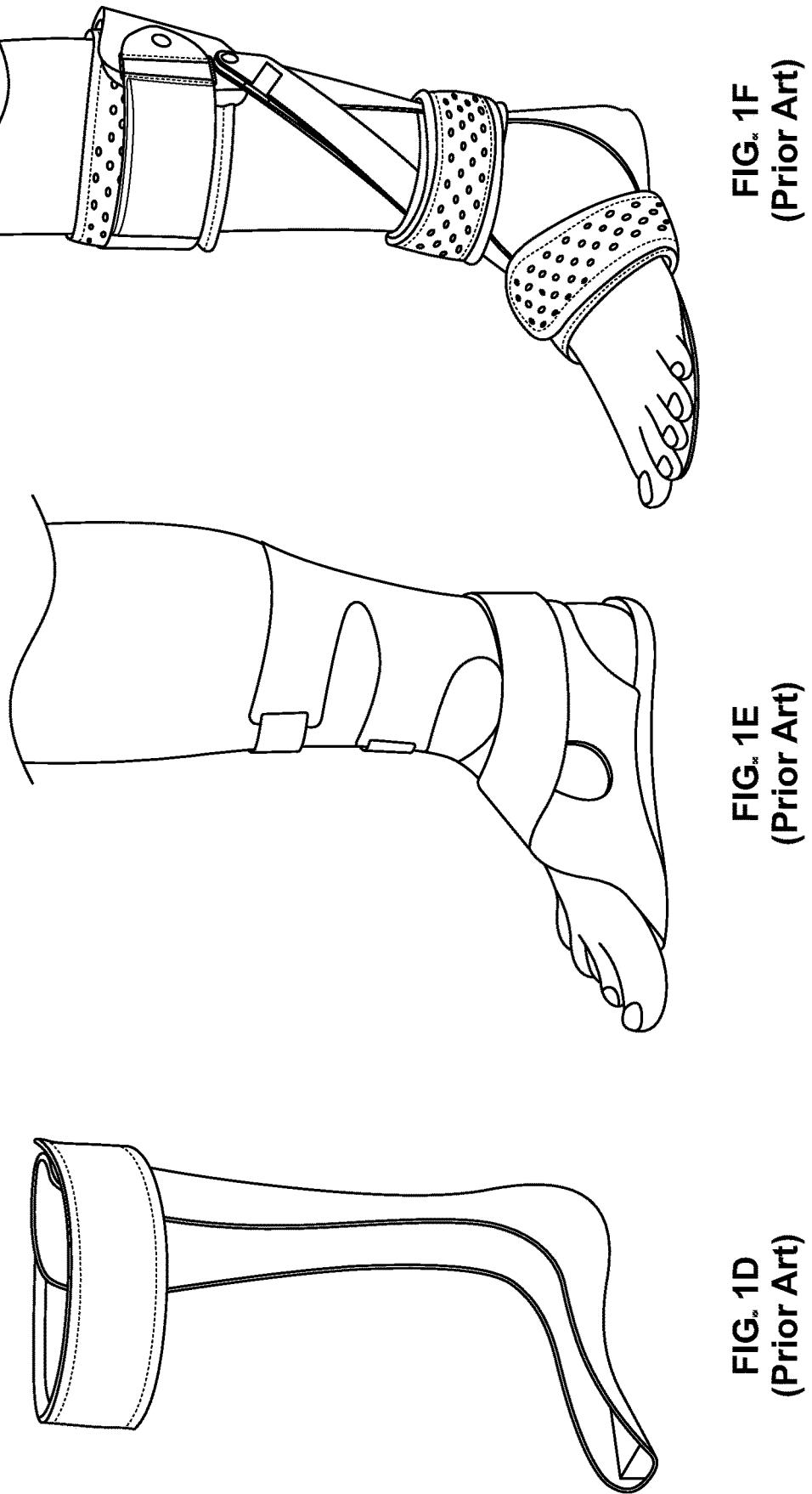
Figures 1G, 1H:
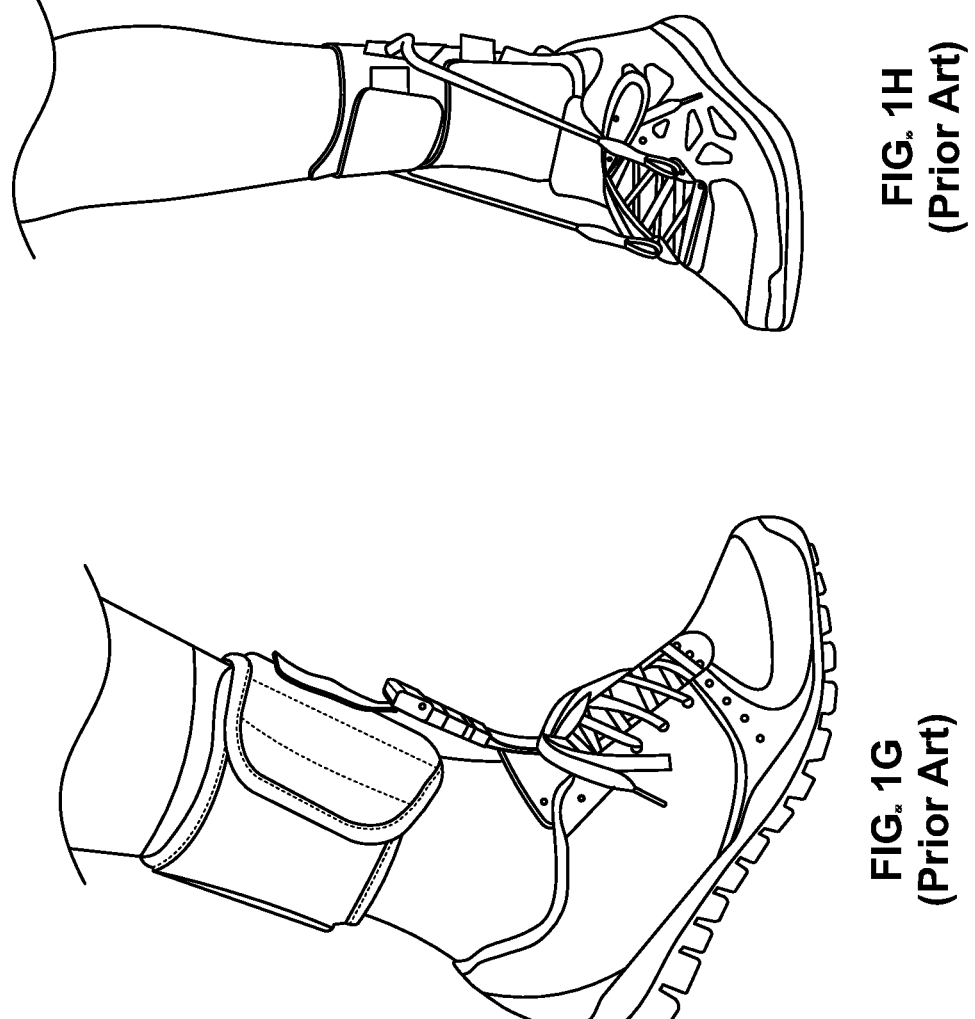

Aspects of the invention are described herein with reference to care and management of certain medical conditions among post-stroke patients, such as foot drop. It will be understood by one of ordinary skill in the art that the exemplary AFOs described herein are not limited to specific patients who have foot drop or to specific care and management protocols. Other types of patients or medical treatment plans suitable for use with the disclosed AFOs will be known to one of ordinary skill in the art from the description herein.

A "target wearer" as described herein is a wearer having characteristics at least within a known or expected range of values, which may be actual values as measured, or expected ranges based upon birth gender, height, weight, and other physiological factors. It should be understood that designs intended for a target wearer may be sized to accommodate a specific individual wearer or a spectrum of wearers having physiological measurements within the expected ranges of values.

While the exemplary embodiments of the invention are described herein with respect to certain medical conditions, such as foot drop, it will be understood that the invention is not so limited. Suitable applications for systems of the present invention include, for example, AFOs for use in athletic gear, military gear, police gear, and construction gear. Other suitable applications will be readily understood by one of ordinary skill in the art from the description herein.

As part of the design process leading to the embodiments of the present invention, qualitative research was performed to determine the needs and wants from unbiased, primary sources. This qualitative research was exploratory in nature and followed a user-centered approach. Seven interviews were conducted, recorded, and analyzed using a Grounded Theory Framework. Exemplary questions were asked focusing on the user-centered feedback on the form and function of subject AFOs.

The AFO users and the primary care givers were asked to participate in this qualitative research. A total of seven interviews were conducted with 12 total participants (64.29±8.81 years). Each participant had previously experienced a hemiparesis stroke and was prescribed an AFO for stroke-related mobility issues. Analysis revealed several major themes and concepts sorted into two groups, medical purpose or user perspective. These themes and concepts were further sorted and prioritized by frequency in interviews and functional needs. Lastly, the themes and concepts were turned into "needs" and "wants," and categorized into user perspective and biomechanical standards, as indicated below in Table 1. The exemplary AFO embodiments as further described herein were developed to provide improvements over the prior art with respect to one or more of these needs and wants.

TABLE 1

| Exemplary Needs and Wants | | |
| --- | --- | --- |
| | Needs | Wants |
| User Perspective | Increase mobility of user Increase stability and security of ankle Easy to operate properly Have high durability | One handed donning mechanism Discrete design Different aesthetic options Waterproof Not require additional purchases Wear a variety of shoe types Sleek design Affordable |
| Biomechanical Standards | Function as good or better than existing commercial AFO Safe Safe materials Able to withstand forces applied by user Prevents involuntary motion of the foot-ankle region | |

Figure 2:
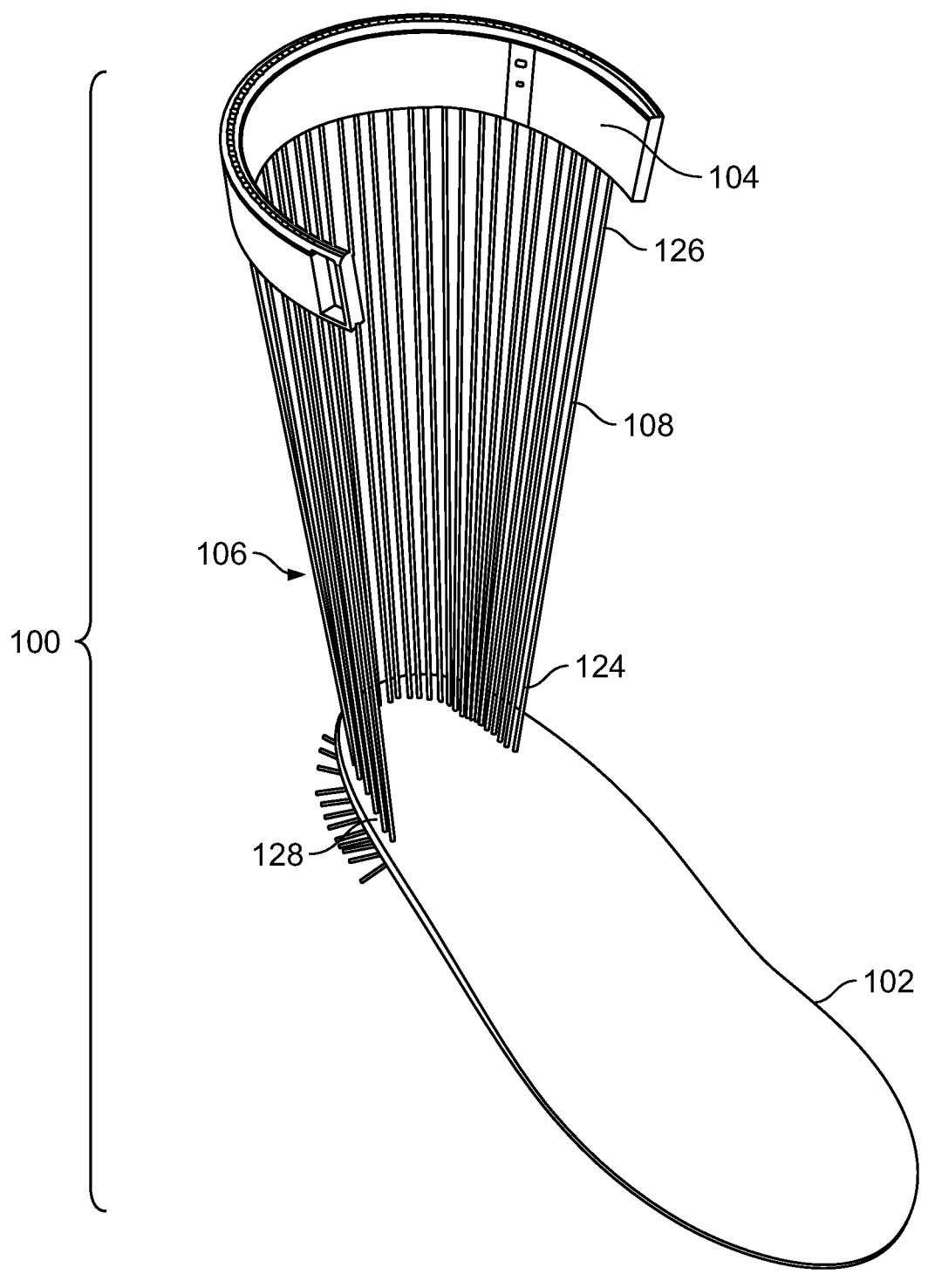
FIG. 2 is an image depicting an exemplary AFO embodiment of the invention.

FIG. 2 illustrates an example AFO 100 in accordance with aspects of the present invention. AFO 100 is usable for proper care of injuries and impairments related to the foot and/or ankle. The AFO 100 can be adjusted to provide proper care of various target wearers (e.g. patients, the elderly, etc.) and to adapt to various scenarios (e.g. performing day-to-day activities, during a physical therapy session, etc.).

In general, AFO 100 is configured to be worn by a target wearer on the wearer's foot and shank. AFO 100 generally includes a foot plate 102, a flexible cuff 104, and a strut assembly 106 comprising a plurality of metal wires 108 connecting the foot plate 102 to the cuff 104. The AFO 100 may be adapted to provide a custom fit to the target wearer, while avoiding the excessive cost and casting process associated with custom orthotics or orthopedic devices. Additional details of AFO 100 are described below.

Figures 3, 4:
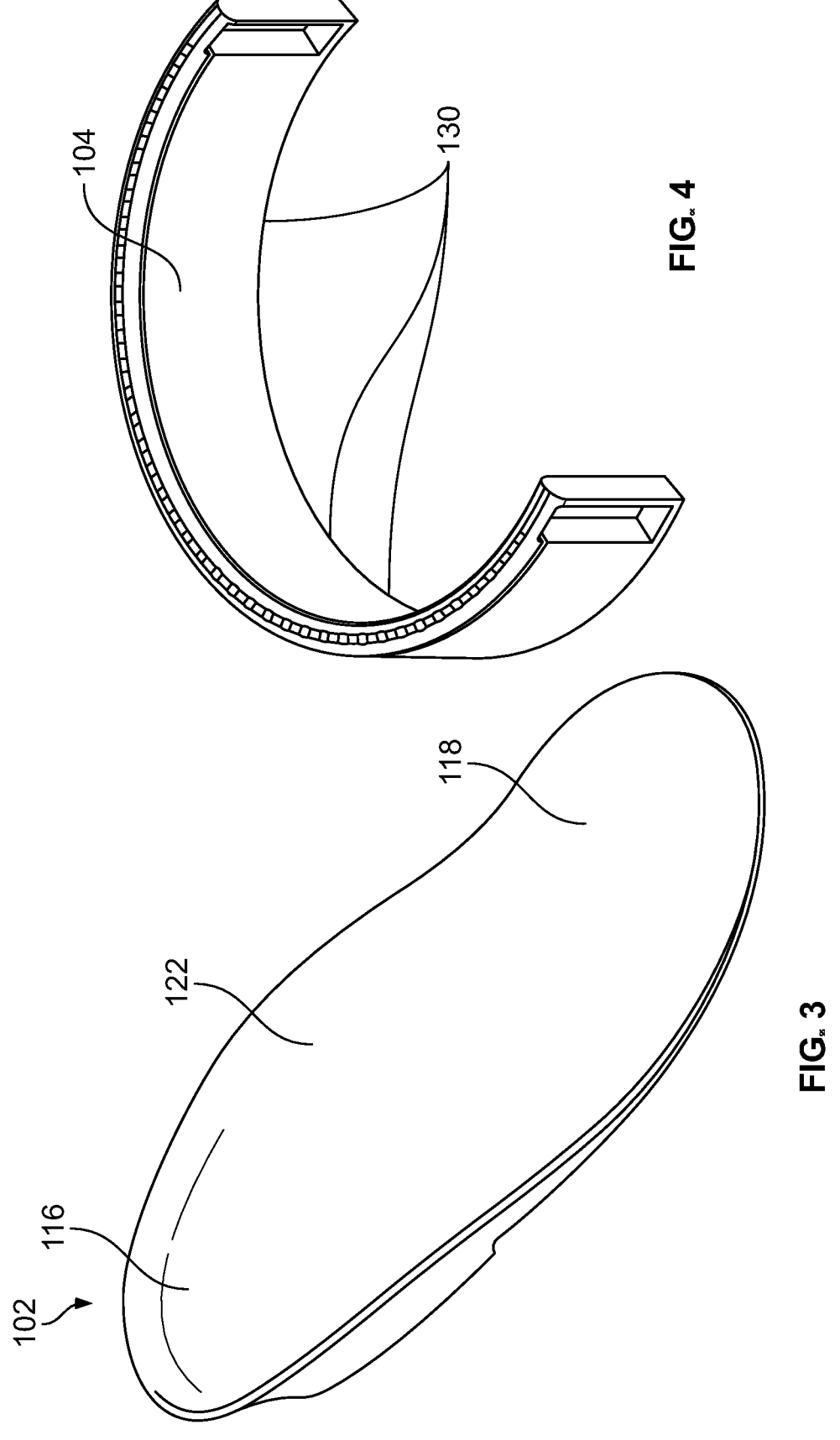
FIG. 3 is an image depicting an exemplary foot plate of the embodiment of FIG. 2.
FIG. 4 is an image depicting an exemplary cuff of the embodiment of FIG. 2.
Figures 5A, 5B:
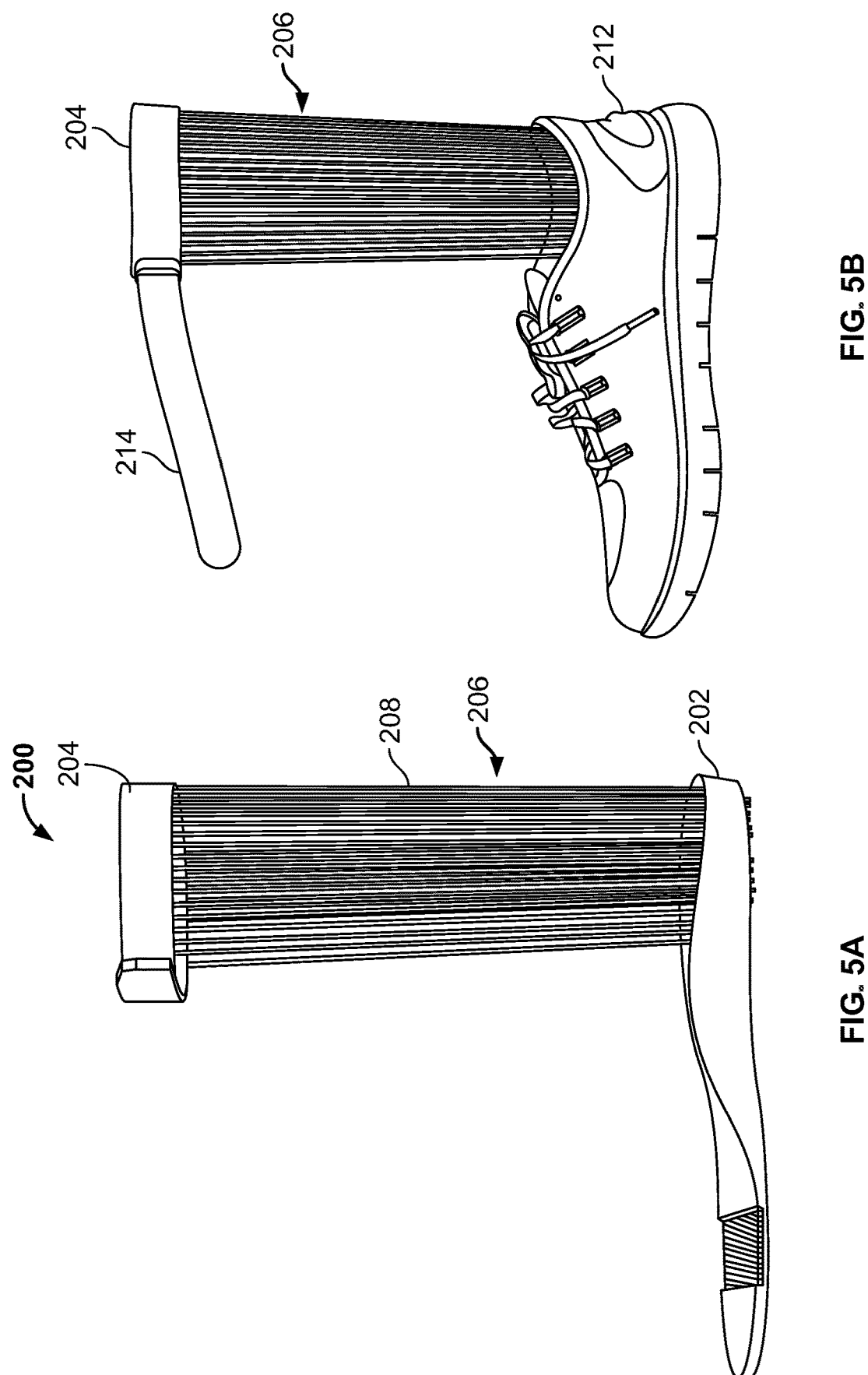
FIG. 5A is an image depicting another exemplary AFO embodiment of the invention.
FIGS. 5B-5D are images depicting integration of the exemplary AFO of FIG. 5A with a shoe.
Figures 5C, 5D:
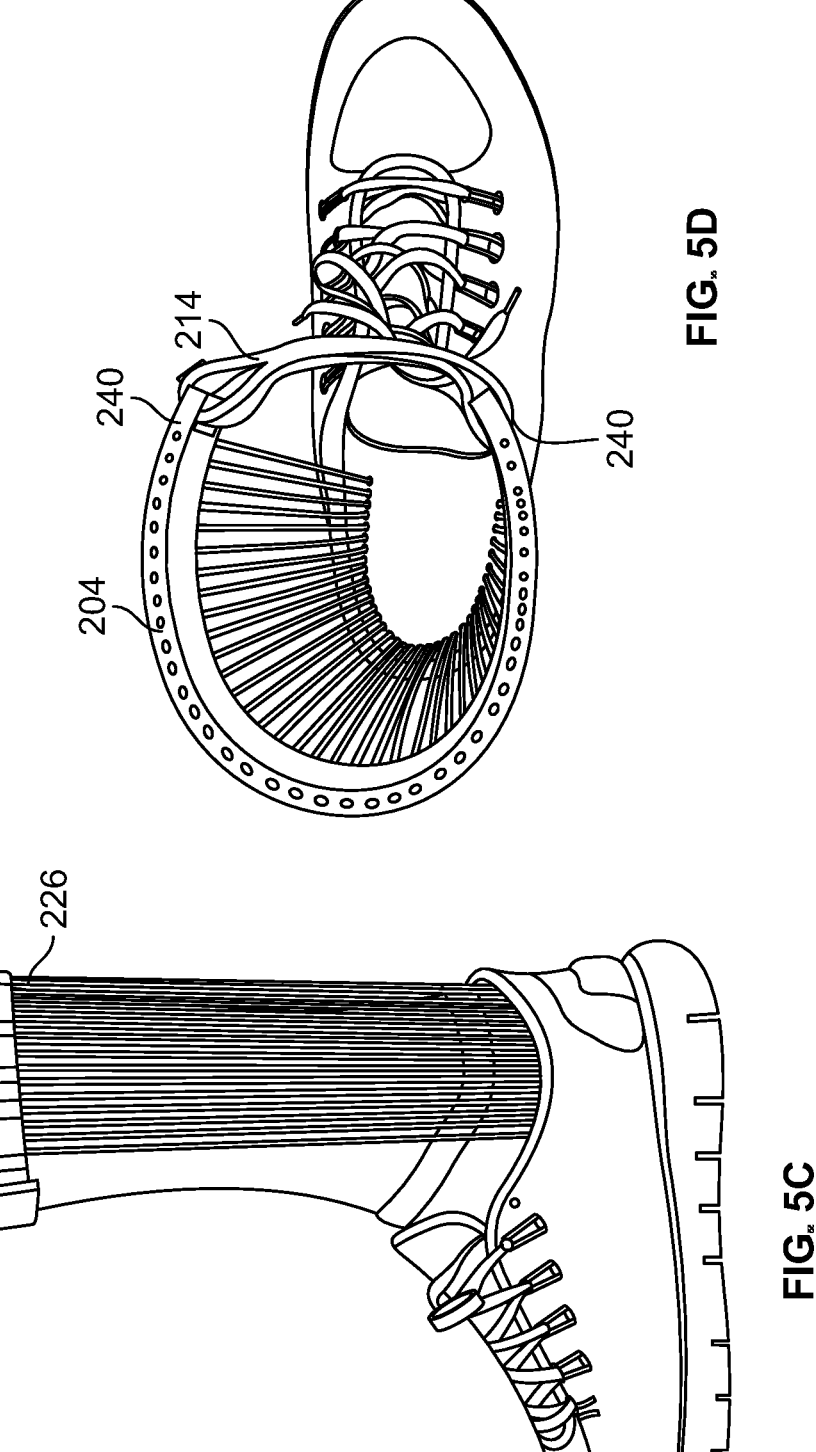

As illustrated in FIGS. 2 and 3, the AFO 100 comprises the foot plate 102, which may be configured to be lightweight, but durable. In an exemplary embodiment, the foot plate 102 may have a foot bed 122 contoured to underlie at least a portion of the foot of the wearer. In an exemplary embodiment, the foot bed 122 is configured to completely underlie the foot of the wearer, such that when integrated with a shoe (as shown in FIGS. 5B-5D), the foot bed 122 corresponds to an insole of the shoe. In a first exemplary embodiment, the foot bed 122 may have a front edge that does not extend substantially forward beyond the target wearer's toes (i.e. no more than a typical insole may extend forward beyond the wearer's toes in a shoe that is considered a proper fit for the target wearer). Additionally or optionally, the rear edge of the foot bed 122 does not extend substantially rearward beyond the heel of the target wearer's foot (i.e. no more than a typical insole may extend rearward beyond the wearer's heel in a shoe that is considered a proper fit for the target wearer). In summary, the foot bed does not extend in any direction beyond the inner periphery of where the upper of the shoe lies adjacent to the insole of the shoe into which the foot bed 122 is fitted to be integrated. In a second exemplary embodiment, the foot bed 122 may have a front edge that does not extend more than one inch beyond the target wearer's toes. Additionally or optionally, a rear edge of the foot bed 122 does not extend more than one inch beyond the heel of the target wearer's foot. Exemplary embodiments may have a margin between the toes/heel of the wearer and the edges of the footbed sized anywhere between the first and second embodiments. The invention is not limited to any particular margin between the toes/heel of the wearer and the edges of the footbed.

Further, the foot plate 102 is ergonomically designed to be easily integrated within the target wearer's shoe, particularly on the insole of the target wearer's shoe (as best shown, for example, in FIGS. 5B-5D). This ergonomic design can be achieved by having a contoured foot bed 122, for example. The contoured surface of the foot bed 122 may be customizable based on the anatomy and/or physiological characteristics of the target wearer (e.g. patient, the elderly, etc.). Providing a custom-fitted foot plate 102 is configured to achieve ankle stabilization and simultaneously allow ambulation. As used herein and throughout the specification, the term "ambulation" may encompass several fundamental forms of movement, including but not limited to sitting, standing, walking, turning, as well as climbing steps & ramps. In addition, providing a custom fit can desirably reduce the size and increase the comfortability of the AFO 100.

In one non-limiting example, the use of 3-dimensional (3D) printing techniques can permit at least the foot plate 102 to be custom fitted to the target wearer's foot and offer a completely customizable AFO 100, without relying on standard and expensive casting techniques. Forming the foot plate 102 with the use of 3D printing techniques can offer a custom fit, where multiple iterations and sizing alterations can be made relatively quickly and at a low cost. As used herein and throughout the specification, the term "custom fit" is not limited to a user-by-user (e.g. target wearer) basis, but can also refer to providing a relatively smaller number of standard incremental sizes (S, M, L, XL, 2XL) of the AFO 100, which correspond to standard shoe sizes, not limited to any particular standard. As is known in the art, different countries/regions have different generally-accepted length and width size standards, which differ for men and women, and may be expressed on an alphanumeric scale. The AFO 100 of a standard incremental size (e.g. XS, or Ladies US size 4) may provide additional customization (or further custom fit) by including at least one adjustable component (e.g. level of arch support provided). One skilled in the art would understand from the description herein that the adjustable component may be configured for permitting adjustments that result in more individualized or custom fit.

In particular, the contours of the foot plate 102 having a foot bed 122, may have a custom fit by accepting a plurality of customization inputs. The customization inputs may comprise a plurality of parameters corresponding to a foot of the wearer. In an exemplary method, the foot plate 102 may have a custom fit by digitally capturing an image of the foot (e.g., using a 3D scanned image of the foot) and then providing a size and contour of the foot plate 102 based on this digital model. One skilled in the art would understand from the description herein that the digital capture process may include use of a 3D scanning or imaging program. After digitally capturing the image of the foot of the wearer, the digital image or model is subsequently converted into a file usable for a 3D printing technique for constructing the customized foot plate 102. In another exemplary embodiment, the customization inputs may comprise a plurality of parameters corresponding to an insole of the wearer. In an exemplary method, the foot plate 102 may have a custom fit by providing an insole of a shoe of the wearer and then providing a size and contour of the foot plate 102 based on measurement and evaluation of the insole. After assessing the insole of the shoe of the wearer, a digital image or model is subsequently constructed and converted into a file usable for a 3D printing technique for constructing the customized foot plate 102.

The 3D printing technique may comprise steps of using a 3D printer, such as ZMorph 3D Printer, as described and designed by ZMorph S. A. of Wroclaw, Poland, and using a 3D printing element, such as for example, (i) a polylactic-acid (PLA) biopolymer, such as the MatterHackers PRO Series PLA, as designed and described by MatterHackers, Inc. of Lake Forest, California, (ii) a thermoplastic polymer, including a thermoplastic urethane (TPU) such as NinjaTek Armadillo® 3D PRINTER FILAMENT, as designed and described by Fenner Inc. of Manheim, Pennsylvania having a Shore hardness of 75D ("Armadillo"), (iii) a thermoplastic polymer, such as the NinjaTek FlexFill (NINJAFLEX® 3D PRINTER FILAMENT), as designed and described by Fenner Inc. of Manheim, Pennsylvania, which is a TPU with a Shore hardness of 85A ("NinjaFlex"), or a combination thereof. The material properties of the Armadillo polymer was desirable for the foot plate 102 due to its high durability and impact resistance.

In an exemplary embodiment, the foot plate 102 may be constructed from Armadillo polymer. Additionally or optionally, the cuff 104 may be constructed from NinjaFlex polymer. The material properties of Armadillo polymer were discovered to be desirable for the foot plate 102, such that foot plate 102 is sufficiently strong and durable to withstand the stress related to ambulation of the target wearer, for example. The material properties of NinjaFlex polymer were discovered to be desirable for the cuff 104, such that cuff 104 increases the target wearer's comfort during use of AFO 100 and/or is sufficiently flexible to allow ambulation of the target wearer.

In an exemplary embodiment, the foot plate 102 and/or cuff 104 may each be constructed from a combination of Armadillo and NinjaFlex polymers. The material properties of a combination of Armadillo and NinjaFlex polymers was discovered to be desirable for the foot plate 102 and the cuff 104 because the resulting material is sufficiently strong and durable to be worn, but still soft and flexible enough to be comfortable. Additionally or optionally, the cuff 104 may be constructed from a combination of Armadillo and NinjaFlex.

However, it should be understood that the above-discussed materials and ratio of materials used for the construction of the foot plate 102 and/or the cuff 104 are not intended to be limiting. Other 3D printers and 3D printing elements having the same characteristics or resulting in the same desired characteristics for AFO 100 will be known to one of ordinary skill in the art from the description herein.

Referring now to FIG. 3, the foot plate 102 includes a front foot portion 118 and a heel portion 116. In the area between the front foot portion 118 and the heel portion 116 may be a raised or elevated surface corresponding to an arch of the target wearer. This helps provide the strong structural integrity desired to provide cradling support, comfort, and stability during ambulation of the target wearer of the AFO 100, as well as help support the wearer's body weight while standing. In addition, a custom-fit foot plate 102 may be contoured (e.g. to define a flexible posterior foot plate leaf spring) to help the target wearer of the AFO 100 propel forward when moving, such as walking or running, thereby increasing overall mobility of the target wearer of the AFO 100. One skilled in the art would understand that the contours of foot plate 102 having foot bed 122 may vary based on one or more physiological characteristics of the target wearer, such as height and shoe size.

As shown in FIG. 2 and FIG. 4, the flexible cuff 104 is configured to wrap around at least a portion of the shank of the wearer (as best shown in FIGS. 5B-5D). In an exemplary embodiment, the cuff 104 may be connected to the foot plate 102 via the strut assembly 106. The strut assembly 106 comprises a plurality of metal wires 108, each of which includes a foot plate end portion 124 and a cuff end portion 126. Generally, assembly of the AFO 100 includes very simple and easy-to-follow steps, thereby decreasing potential points of user failure of AFO 100. The respective proximal ends of the cuff end portions 126 are each inserted into respective attachments points 130 (discussed below) of cuff 104. The respective distal ends of the foot plate end portions 124 are each inserted into plurality of openings 128 (discussed below) of foot plate 102. In terms of integrating the AFO 100 with the shoe of the wearer, the foot plate 102 is configured to replace the insole of the shoe of the wearer (and therefore does not require a larger size shoe to be purchased to accommodate the foot plate 102 and use of the AFO 100).

In this configuration, the cuff 104 comprises attachment points 130 for receiving the respective proximal ends of the cuff end portions 126 of the plurality of metal wires 108. The respective proximal ends of the cuff end portions 126 may be secured (i.e. so that the metal wires 108 do not inadvertently slip out or separate from the attachment point 130 of the cuff 104) via known attachment means, such as a press fit between the wire and the holes in the cuff for receiving the wires, which holes are formed at a sufficiently lesser diameter than the diameters of the wires to provide a desirable level of resistance. Other attachment options may also be used, and the invention is not limited to any particular attachment mechanism. Correspondingly, the heel portion 116 includes a plurality of openings 128 configured to receive the distal ends of the foot plate end portion 124 of the plurality of metal wires (as shown in FIG. 2). In a non-limiting example, the plurality of openings 128 each may connect to one of a series of pockets disposed adjacent each other (as described in more detail with respect to FIG. 5F) and may be spaced apart corresponding to a curve (arc length) around the heel of the target wearer. The distal ends of the foot plate end portion 124 may be secured in the openings 128 by insertion in the pockets, as described herein below, or the distal ends of the foot plate end portion 124 may be nested in respective recesses defined by the foot plate 102 and manipulated (i.e. bent) to extend laterally outward relative to the foot plate 102 (in which case pockets may be formed extending laterally outward from the openings). Further, the number of openings 128 may correspond to the number of metal wires 108 required to connect the cuff 104 to the foot plate 102, such that the foot and ankle of the target wearer are stabilized, while simultaneously allowing for ambulation. In an exemplary embodiment, 39 metal wires are required for AFO 100 to provide the desired stabilization and ambulation. Thus, during assembly of the foot plate 102 and the cuff 104, the respective distal end of each foot plate end portion 124 of the 39 metal wires is received by one of the respective openings 128. However, it should be understood that the illustrated number and locations of where the foot plate end portions 124 are disposed relative to the foot plate 102 and the locations of the attachment points 130 of the cuff 104, are not intended to be limiting, such that they may be positioned to accommodate one or more physiological characteristics of the target wearer (e.g. height, shoe size, etc.).

In an exemplary embodiment, the plurality of wires 108 of the strut assembly 106 may comprise piano wires. Piano wires, as the name implies, are specialized wires for use in piano strings typically. In a non-limiting example, piano wire is a type 304 stainless steel spring wire. The material properties of a piano wire were discovered to be desirable for providing ankle and foot stabilization, and for allowing ambulation. In particular, the high tensile strength and high elastic property of the piano wire makes it ideal for high-stress applications (such as required for ambulation), energy storage, and durability. The number, density, and/or arc length of the piano wires may be sufficient to secure the foot plate 102 to the cuff 104, without being overly stiff, such that the mobility and ambulation of the target wearer is permitted. In an exemplary embodiment, the strut assembly 106 further comprises textile or fabric material interwoven with the plurality of metal wires 108 to provide increased comfort or more appealing aesthetics of the AFO 100.

In an exemplary embodiment, the plurality of metal wires 108 includes a first group of one or more wires having a first set of material properties and a second group of one or more wires having a second set of material properties different than the first set of material properties. The first group of wires may correspond to the AFO 100 used for the left foot of the target wearer and the second group of wires may correspond to the AFO 100 used for the right foot of the target wearer, or alternatively, the first group of wires and second group of wires may be in the same AFO 100 for the left or right foot of the target wearer. The first group of wires may have a different thickness (as indicated by diameter, for example), than that of the second group of wires. Additionally or optionally, the first group of wires may comprise a different alloy, a different annealing process, a different heat treatment, or combination thereof, than that of the second group of wires. In another exemplary embodiment, the plurality of metal wires 108 may have uniform material properties, such as having a thickness or diameter of 0.075 inches. Although the plurality of wires 108 are described as belonging to one of the first or second group, one skilled in the art would understand from the description herein that the invention is not so limited, and may include more than two groups of wires having the same or different material properties and these plural groups may be present in one or both AFOs 100 for use with the left and/or right foot of the target wearer, without departing from the spirit and scope of the invention. In an exemplary embodiment, the differences or similarities of material properties of the plurality of wires 108 may be configured to accommodate one or more physiological characteristics of the target wearer (e.g. height, shoe size, etc.), or a specific characteristic of the target wearer's medical conditions or gait abnormalities.

Another embodiment of the AFO 100 according to the present invention is illustrated in FIGS. 5A-5G. The components of this embodiment, such as AFO 200, generally correspond to the components of AFO 100 (i.e. foot plate 202 connects to cuff 204 via strut assembly 206 of metal wires 208). However, this second embodiment differs from the first embodiment described above in some respects.

In one example, as shown in FIG. 5E, the front foot portion 218 may comprise a plurality of ridges or grooves 232. The plurality of ridges 232 may be included for providing a relatively greater flexibility at the front foot portion 218 relative to the heel portion 216 of the footbed 222. In an exemplary embodiment, the plurality of ridges 232 are positioned to correspond to the metatarsal region of the target wearer. When walking with a normal gait (e.g. without a foot drop condition), the foot naturally bends at the metatarsal region. Accordingly, the foot plate 102 comprises material that is less brittle (than other components of the AFO 200, such as the cuff 204) and more flexible to promote normal gait. In addition, the plurality of ridges 232 may be configured to keep the front foot portion 218 elevated (or pull upward) to prevent toes from dragging, or to counter any inclination to have toes drag, because of the weakness of the plantar flexors and the dorsi flexors of the affected foot. Further, the plurality of ridges 232 may be configured to promote the natural heel-to-toe (e.g. forward) rolling of the foot, thereby countering the inclination to drag the toes or shuffle the feet because of the weakness of the plantar flexors and/or dorsi flexors of the affected foot. Still further, the plurality of ridges 232 allow the foot plate 202 to bend without applying too much stress to AFO 200, which could undesirably cause a safety hazard, e.g. the foot plate 202 breaks or shatters during or after use by the target wearer.

Additionally or optionally, as shown in FIGS. 5E and 5G, the front foot portion 218 comprises a flexible region between a proximal portion 234 of the foot plate 202 and a distal portion 236 of the foot plate 202. This flexible region may be configured to have a range of bendability between a resting position and a flexed position (FIG. 5G), wherein the flexed position comprises an included angle (x°) of 70° or less between a plane defined by the proximal portion 234 and a plane defined by the distal portion 236. One skilled in the art would understand from the description herein that the flexed position may also include an angle (x°) of 0° or less between the proximal portion 234 and the distal portion 236, such as during ascending or descending the stairs. The resting position may comprise an angle of (x°) of 0° or near (e.g. within +/−5°) of 0°. In a non-limiting example, the flexible region comprises the plurality of ridges 232, such that the flexible region corresponds to the metatarsal region of the wearer, where the foot naturally bends when walking with a normal gait (e.g. without a foot drop condition). In an exemplary embodiment, the flexible region comprises a first set of material properties and a less flexible region of the foot plate 202 has a second set of material properties that are different than the first set of material properties. Material properties include, but are not limited to, properties related to flexibility. This non-uniformity in flexibility between the front foot portion 218 and the less flexible region of the foot plate 202 can facilitate ambulation and mobility of the wearer (e.g. walking, running, etc.), while simultaneously stabilizing the foot and ankle joint.

As best illustrated in FIG. 5F, which depicts an underside 220 of the foot plate 202, the distal end of foot plate end portion 224 of each respective wire 208 of the strut assembly 206 may be positioned within one of the plurality of pockets 238. The pockets 238, each of which comprises an area inset into the thickness of the foot plate and extending a medial distance from each opening 228, receives the distal end of the foot plate end portion 224 of each wire. Accordingly, a portion of the foot plate end portion 224 of the respective metal wires of the strut assembly 206 are manipulated and tucked into respective pockets 238 disposed along the underside 220 of the foot plate 202, i.e. a bottom surface (surface opposite the foot of the target wearer) of the foot plate 202. This configuration desirably allows use of the piano wires 108, while providing reduced damage to the footwear (when the foot plate 202 is integrated with a shoe 212 of the wearer, as best shown in FIG. 58), and provides increased comfort to the target wearer. In an exemplary embodiment, the respective distal ends of the foot plate end portion 224 of each wire 208 may define an included angle of up to 90° relative to a line defined by the respective metal wire 208 between the foot plate end portion 224 and the cuff end portion 226. As illustrated in FIG. 5F, the distal ~1 cm of the foot plate end portions 224 may be received in pockets 238 after being bent at an inflection point of an included angle of up to 90° to minimize the possibility of the piano wire 208 of the strut assembly 206 from inadvertently slipping out during or after use.

In still another example, as shown in FIGS. 5A-5D, the cuff 204 comprises at least one adjustable fastening strap 214 for securing the cuff 204 to the shank of the wearer. The adjustable fastening strap 214 may comprise a hook and loop type mechanism, e.g. a Velcro® strip, which is configured to loop through a pair of openings 240 defined by opposite end portions of the cuff 204. Additionally or optionally, the strap 214 may include mating magnetic fasteners for securing the strap 214 in a desired configuration and in a desired tightness for securing the AFO 100 against the shank of the target wearer, and/or providing the desired ankle and foot stability during ambulation. In an exemplary embodiment, the strap 214 may comprise mating magnetic fasteners, such as the closure systems described and designed by FIDLOCK GmBH of Hannover, Germany. Additionally or optionally, the edges of the cuff 204 may comprise rounded/filleted edges to avoid excessive chaffing against the skin of the target wearer, thereby providing increased comfort.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An ankle-foot orthosis configured to be worn by a wearer, the wearer having a foot and a shank, the ankle-foot orthosis comprising:
   a foot plate having a foot bed contoured to underlie the foot of the wearer, the foot plate having a heel portion and a front foot portion;
   a flexible cuff configured to wrap around at least a portion of the shank of the wearer;
   a strut assembly comprising a plurality of metal wires connecting the foot plate to the cuff; and
   wherein the heel portion of the foot plate has a plurality of pockets each disposed in an underside surface of the heel portion and each configured to receive a distal end portion of one of the plurality of metal wires.

2. The ankle-foot orthosis of claim 1, further comprising a plurality of ridges at a front foot portion of the foot plate for providing a relatively greater flexibility at the front foot portion relative to a heel portion of the foot plate.

3. The ankle-foot orthosis of claim 2, wherein the front foot portion comprises a flexible region between a proximal portion of the foot plate and a distal portion of the foot plate, the flexible region having a range of bendability between a resting position and a flexed position, and wherein the flexed position comprises an included angle of 70° or less between the proximal portion and the distal portion.

4. The ankle-foot orthosis of claim 3, wherein the flexible region includes the plurality of ridges and corresponds to the wearer's metatarsal region.

5. The ankle-foot orthosis of claim 1, further comprising at least one adjustable fastening strap for securing the cuff to the shank of the wearer and configured to loop through a pair of openings defined by opposite end portions of the cuff.

6. The ankle-foot orthosis of claim 5, wherein the strap includes mating magnetic fasteners for securing the strap in a desired configuration.

7. The ankle-foot orthosis of claim 1, wherein the plurality of metal wires includes a first group of wires having a first set of material properties and a second group of wires having a second set of material properties different than the first set of material properties.

8. A method of making the ankle-foot orthosis of claim 7, the method comprising the steps of:

accepting a plurality of customization inputs, the input comprising a plurality of parameters corresponding to a foot of the target wearer;

constructing a digital model for characterizing the foot plate;

transmitting the digital model to a computer aided manufacturing process for automatically fabricating the ankle-foot orthosis.

9. The ankle-foot orthosis of claim 1, wherein at least the foot plate is sized to be inserted in a shoe of the target wearer.

10. A method of making the ankle-foot orthosis of claim 9, the method comprising the steps of:

providing an insole of the shoe of the target wearer;

accepting a plurality of customization inputs, the input comprising a plurality of parameters corresponding to the insole;

constructing a digital model for characterizing the foot plate based upon the insole; and transmitting the digital model to a computer aided manufacturing process for automatically fabricating the ankle-foot orthosis.

11. The ankle-foot orthosis of claim 1, wherein each of the plurality of metal wires comprises piano wire.

12. The ankle-foot orthosis of claim 1, wherein the distal end portion of each respective wire of the plurality of metal wires is positioned within one of the plurality of pockets and defines an included angle of up to 90 relative to a line defined by a portion of the respective metal wire extending between the foot plate and the cuff.

13. The ankle-foot orthosis of claim 1, wherein the cuff comprises attachment points for receiving respective proximal end portions of the plurality of metal wires.

14. The ankle-foot orthosis of claim 1, wherein the strut assembly comprises textile or fabric material interwoven with the plurality of metal wires.

\* \* \* \* \*